US012663408B2

(12) United States Patent
Tamada et al.

(10) Patent No.: US 12,663,408 B2
(45) Date of Patent: Jun. 23, 2026

(54) SPATTER DETECTION METHOD AND METHOD FOR MANUFACTURING WELDED MEMBER

(71) Applicant: TOYOTA JIDOSHA KABUSHIKI KAISHA, Toyota (JP)

(72) Inventors: Yosuke Tamada, Toyota (JP); Tomoko Ogasahara, Nagoya (JP); Tomohiko Sekiguchi, Nagakute (JP)

(73) Assignee: TOYOTA JIDOSHA KABUSHIKI KAISHA, Toyota (JP)

( * ) Notice: Subject to any disclaimer, the term of this patent is extended or adjusted under 35 U.S.C. 154(b) by 288 days.

(21) Appl. No.: 18/632,429

(22) Filed: Apr. 11, 2024

(65) Prior Publication Data

US 2024/0353387 A1      Oct. 24, 2024

(30) Foreign Application Priority Data

Apr. 19, 2023      (JP) ................................. 2023-068665

(51) Int. Cl.
    *G01N 33/207*        (2019.01)
    *B23K 11/11*         (2006.01)
    *B23K 11/16*         (2006.01)

(52) U.S. Cl.
    CPC ............ *G01N 33/207* (2019.01); *B23K 11/16* (2013.01); *B23K 11/115* (2013.01)

(58) Field of Classification Search
    CPC ..... B23K 11/115; B23K 11/16; B23K 31/125; B23K 11/11; B23K 11/0026; B23K 11/185; B23K 11/20; B23K 11/30; B23K 11/24; B23K 11/3009; B23K 11/257; G01N 33/207
    USPC ................................ 73/865.8, 850, 149, 861
    See application file for complete search history.

(56) References Cited

FOREIGN PATENT DOCUMENTS

| JP | 2008105041 A | * | 5/2008 | |
| JP | 2020093287 A | * | 6/2020 | ........... B23K 11/257 |
| JP | 2024-034715 A | | 3/2024 | |

* cited by examiner

*Primary Examiner* — John E Breene
*Assistant Examiner* — Truong D Phan
(74) *Attorney, Agent, or Firm* — Sughrue Mion, PLLC

(57)      ABSTRACT

A spatter detection method in which the accuracy of detection of an occurrence of sputter is high, and a method for manufacturing a welded member are provided. A spatter detection method according to the present disclosure is a spatter detection method for detecting an occurrence of sputter in resistance spot welding, the resistance spot welding being welding in which a material to be welded, obtained by stacking a plurality of metal members on one another, is joined by sandwiching the material to be welded between a pair of electrodes and feeding an electric current therethrough, in which the occurrence of sputter is detected based on a change in a volume of a molten part of the material to be welded.

3 Claims, 6 Drawing Sheets

STROKE REFERENCE
POSITION S0

SPATTER DETECTION METHOD AND METHOD FOR MANUFACTURING WELDED MEMBER

CROSS REFERENCE TO RELATED APPLICATIONS

This application is based upon and claims the benefit of priority from Japanese patent application No. 2023-068665, filed on Apr. 19, 2023, the disclosure of which is incorporated herein in its entirety by reference.

BACKGROUND

The present disclosure relates to a spatter detection method and a method for manufacturing a welded member.

In resistance spot welding, when sputter (or sputtering) occurs, the diameter of a nugget decreases, thus making it impossible to achieve satisfactory welding quality. Therefore, technologies for detecting sputter have been developed.

For example, Japanese Unexamined Patent Application Publication No. 2008-105041 discloses a resistance welding method in which resistance welding is carried out by feeding an electric current through a pair of electrodes, and also discloses a method for detecting sputter. In the method for detecting sputter disclosed in Japanese Unexamined Patent Application Publication No. 2008-105041, an occurrence of sputter is detected by detecting a change in the displacement of an electrode, in the voltage between electrodes, or in the resistance between electrodes.

SUMMARY

In the above-described method for detecting an occurrence of sputter disclosed in Japanese Unexamined Patent Application Publication No. 2008-105041, even if sputter occurs, when the size of the sputter is small, there is a possibility that none of the changes in the displacement of an electrode, in the voltage between electrodes, or in the resistance between electrodes can be detected, and therefore the occurrence of the sputter cannot be detected.

The present disclosure has been made in view of such circumstances, and provides a spatter detection method in which the accuracy of detection of an occurrence of sputter is high, and a method for manufacturing a welded member.

A spatter detection method according to the present disclosure is a spatter detection method for detecting an occurrence of sputter in resistance spot welding, the resistance spot welding being welding in which a material to be welded, obtained by stacking a plurality of metal members on one another, is joined by sandwiching the material to be welded between a pair of electrodes and feeding an electric current therethrough, in which the occurrence of sputter is detected based on a change in a volume of a molten part of the material to be welded.

In a spatter detection method according to the present disclosure, an occurrence of sputter is detected by a change in a volume of a molten part of a material to be welded, melted by a pair of electrodes. Therefore, the accuracy of the detection of an occurrence of sputter is high.

Further, the sputter may be detected based on a rate of change at which the volume of the molten part decreases. By the above-described configuration, it is possible to detect an occurrence of sputter from the value of the rate of change at which the volume decreases, and therefore the accuracy of the detection of an occurrence of sputter is high.

Further, the pair of electrodes may further include a first electrode, and a second electrode movable relative to the first electrode in a direction in which the metal members are stacked on one another, and the change in the volume of the molten part may be calculated based on a change in a distance between the first and second electrodes, and a change in an internal stress of the molten part.

By the above-described configuration, it is possible to calculate the change in the volume of the molten part, and therefore the accuracy of the detection of an occurrence of sputter is high.

Note that the change in the volume of the molten part may be calculated by Expression (1), $$E = S + a \times F \tag{1}$$

where E is the change in the volume of the molten part; S is a stroke of the second electrode; a is a distortion conversion coefficient; and F is a pressure between the first and second electrodes.

By the above-described configuration, it is possible to calculate the change in the volume by measuring the stroke of one of the pair of electrodes, which is movable relative to the other electrode, and the pressure between the pair of electrodes, so that the accuracy of the detection of an occurrence of sputter is high.

In a method for manufacturing a welded member according to the present disclosure includes:

performing resistance spot welding for joining a material to be welded, obtained by stacking a plurality of metal members on one another, by sandwiching the material to be welded by a pair of electrodes and feeding an electric current therethrough;

detecting a change in a volume of a molten part of the material to be welded; and detecting an occurrence of sputter in the resistance spot welding based on the change in the volume.

In the method for manufacturing a welded member according to the present disclosure, it is possible to manufacture the welded member while detecting an occurrence of sputter based on the change in the volume of the molten part of the material to be welded, melted by the pair of electrodes.

According to the present disclosure, it is possible to provide a spatter detection method in which the accuracy of detection of an occurrence of sputter is high, and a method for manufacturing a welded member.

The above and other objects, features and advantages of the present disclosure will become more fully understood from the detailed description given hereinbelow and the accompanying drawings which are given by way of illustration only, and thus are not to be considered as limiting the present disclosure.

DESCRIPTION OF EMBODIMENTS

Figure 1:
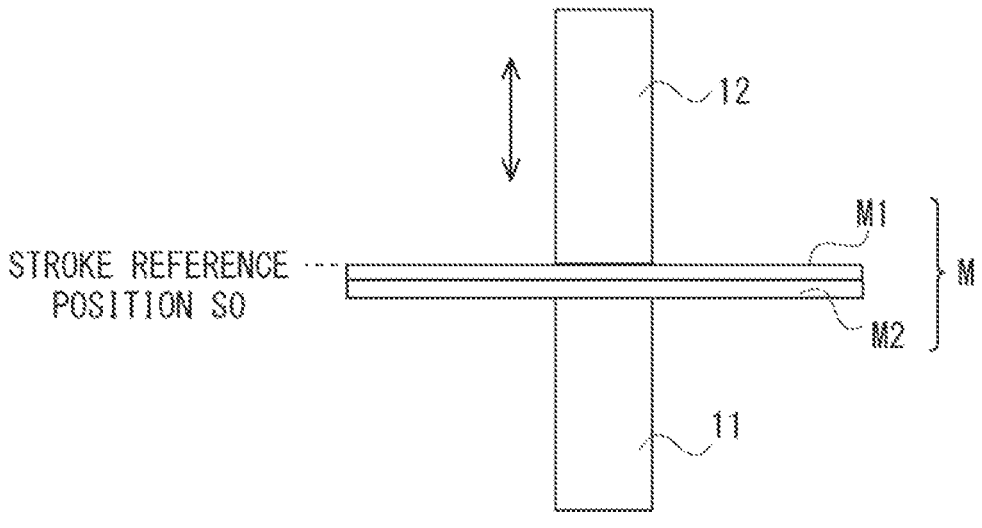
FIG. 1 is a schematic diagram for resistance spot welding.
Figure 1:

The present disclosure will be described hereinafter through embodiments, but the invention according to the claims is not limited to the below-shown embodiments. Further, all the components/structures described in an embodiment are not necessarily essential as means for solving the problem. For clarifying the explanation, the following descriptions and drawings are partially omitted and simplified as appropriate. The same reference numerals (or symbols) are assigned to the same elements throughout the drawings, and redundant descriptions are omitted as appropriate. Note that, needless to say, right-handed xyz-orthogonal coordinates shown in the drawings are shown just for the sake of convenience for explaining the positional relation among components. In general, the z-axis positive direction is the vertically upward direction and the xy-plane is a horizontal plane.

First Embodiment

<Overview of Resistance Spot Welding>

Firstly, an overview of resistance spot welding will be described with reference to FIG. 1. FIG. 1 is a schematic diagram of resistance spot welding.

As shown in FIG. 1, a material to be welded M is formed by stacking metal members M1 and M2 on one another in the z-axis direction. The metal members M1 and M2 are typically plate-like members as shown in FIG. 1, but are not limited to such members. For example, they may be cylindrical members such as flange members. Further, although the material to be welded M is formed by stacking two plate-like metal members M1 and M2 as shown in the example shown in FIG. 1, it may be formed by a plurality (i.e., three or more) of metal members.

As shown in FIG. 1, a pair of electrodes includes a first electrode 11 and a second electrode 12. In the example shown in FIG. 1, the position of the first electrode 11 is fixed, and the second electrode 12 has such a structure that it is movable relative to the first electrode 11 in the stacking direction of the metal members M1 and M2 (i.e., in the z-axis direction).

However, it is not limited to such a structure. That is, the second electrode 12 may have such a structure as described above so that it is movable relative to the first electrode 11 in the stacking direction of the metal members M1 and M2 (i.e., in the z-axis direction). More specifically, the first electrode 11 can move in the stacking direction of the metal members M1 and M2 (i.e., in the z-axis direction) while remaining in contact with the metal member M2. The second electrode 12 may have such a structure that it can move relative to the first electrode 11 according to the movement of the first electrode 11 so that the distance between the first and second electrodes 11 and 12 is kept at a predetermined distance.

In the resistance spot welding, the metal members M1 and M2 are joined with each other by sandwiching the material to be welded M between the first and second electrodes, which constitute a pair of electrodes, and feeding an electric current therethrough (i.e., making an electric current flow through the first and second electrodes). The first and second electrodes press the metal members M1 and M2 in the z-axis direction so that the metal members M1 and M2 do not shift from each other even when the volume of the molten part of the material to be welded M is changed (which will be described later).

<Molten Part>

Figure 2:
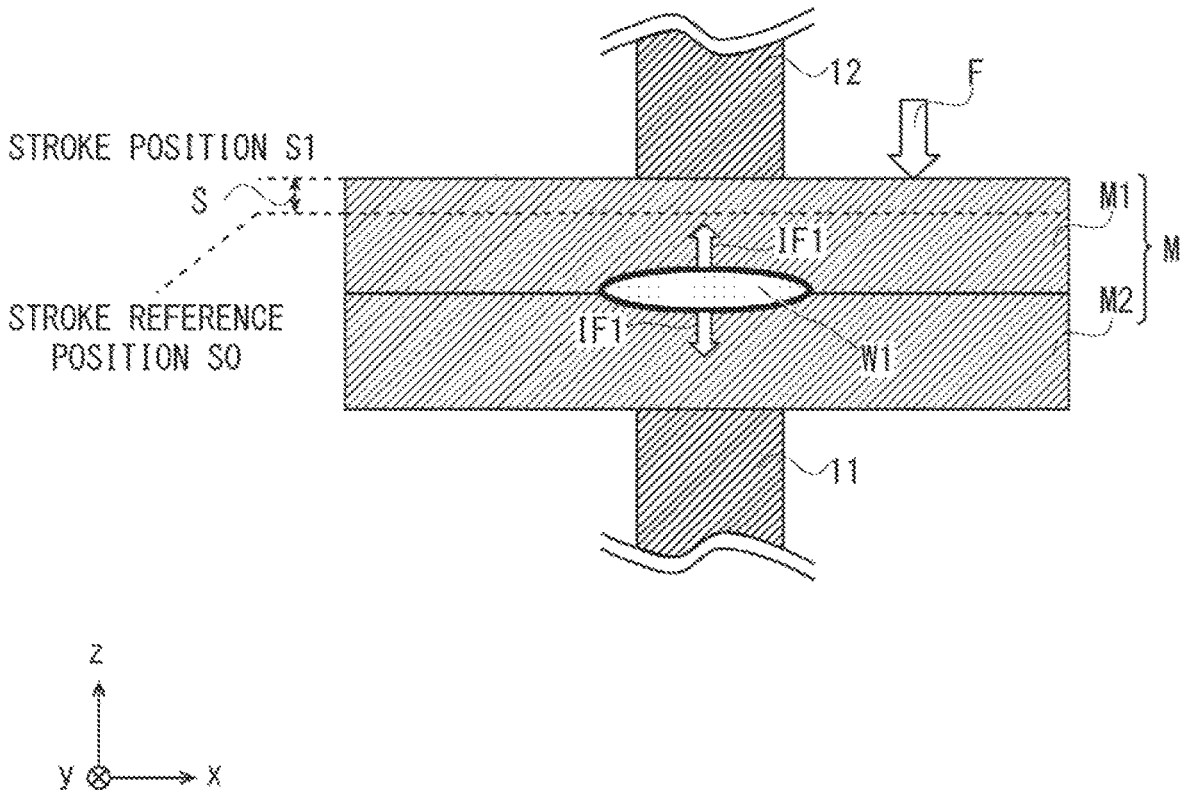
FIG. 2 is a cross-sectional diagram of a material to be welded and a pair of electrodes in the resistance spot welding.

Next, the molten part in the resistance spot welding will be described with reference to FIG. 2. FIG. 2 is a cross-sectional diagram of the material to be welded and the pair of electrodes during the resistance spot welding.

Firstly, the generation (or the formation) of a molten part W1 will be described. As shown in FIG. 2, in the resistance spot welding, by sandwiching the material to be welded M by the first and second electrodes, which constitute a pair of electrodes, and feeding an electric current therethrough (i.e., through the first and second electrodes), a molten part W1 is generated (i.e., formed) between the metal members M1 and M2.

The molten part W1 thermally expands in the resistance spot welding as the electric current flows through the first and second electrodes, and heat is thereby generated therein. As a result, the volume of the molten part W1 increases. Further, when the resistance spot welding is completed, the molten part W1 is cooled by air around it and thermally contracts. As a result, the volume of the molten part W1 decreases. As described above, in the resistance spot welding, the volume of the molten part W1 generated between the metal members M1 and M2 changes.

Next, the change in the volume of the molten part W1 will be described in detail with reference to FIG. 2. The following description will be given on the assumption that the position of the first electrode 11 is fixed and the second electrode 12 can move relative to the first electrode 11 in the stacking direction of the metal members M1 and M2 (i.e., in the z-axis direction). Further, the change in the volume of the molten part W1 will be described by using an example case where the molten part W1 thermally expands.

As shown in FIG. 2, in the resistance spot welding, the molten part W1 thermally expands, so that an internal stress IF1 occurs. The material to be welded M expands in the z-axis positive direction due to this internal stress IF1 of the molten part W1. Further, in the resistance spot welding, since the material to be welded M is sandwiched between the first and second electrodes 11 and 12, a pressure F between the first and second electrodes 11 and 12 and the second electrode acts on the material to be welded M. That is, the pressure F is a force that acts on the material to be welded M to cancel out the internal stress IF1 of the molten part W1. The magnitude of the pressure F per unit area is referred to as a n applied stress.

Note that when the applied stress is equal to the internal stress F1 of the molten part W1, the second electrode 12 is positioned at a stroke reference position S0 shown in FIGS. 1 and 2. The stroke reference position S0 is a position where the second electrode 12 is in contact with the metal member M1 immediately before the resistance spot welding is started.

In contrast, when the internal stress F1 of the molten part W1 is larger than the applied stress, the second electrode 12 moves in the z-axis positive direction, so that the second electrode 12 is positioned at a stroke position S1 shown in FIGS. 1 and 2. Therefore, the stroke S of the second electrode 12 has a value obtained by subtracting the stroke reference position S0 from the stroke position S1.

In other words, an amount (i.e., a distance) by which the material to be welded M expands and thereby pushes up the second electrode 12 in the z-axis positive direction as a result of the thermal expansion of the molten part W1 is the stroke S of the second electrode 12. That is, the stroke S of the second electrode 12 indicates the change in the distance between the first and second electrodes 11 and 12.

As described above, the change in the distance between the first and second electrodes 11 and 12 can be obtained by measuring the stroke S of the second electrode 12. Further, the change in the internal stress of the molten part W1 can be obtained by measuring the pressure F and calculating it from the measured pressure F.

In the resistance spot welding, when the molten part W1 thermally expands, the distance between the first and second electrodes 11 and 12 changes, and the internal stress of the molten part W1 also changes. Therefore, it is possible to calculate the change in the volume of the molten part W1 based on the change in the distance between the first and second electrodes 11 and 12 and the change in the internal stress of the molten part W1.

In the example shown in FIG. 2, the change in the volume of the molten part W1 has been described by using the example case where the molten part W1 thermally expands. However, when the molten part W1 thermally contracts, it is also possible to calculate the change in the volume of the molten part W1 based on the change in the distance between the first and second electrodes 11 and 12 and the change in the internal stress of the molten part W1.

Figure 3:
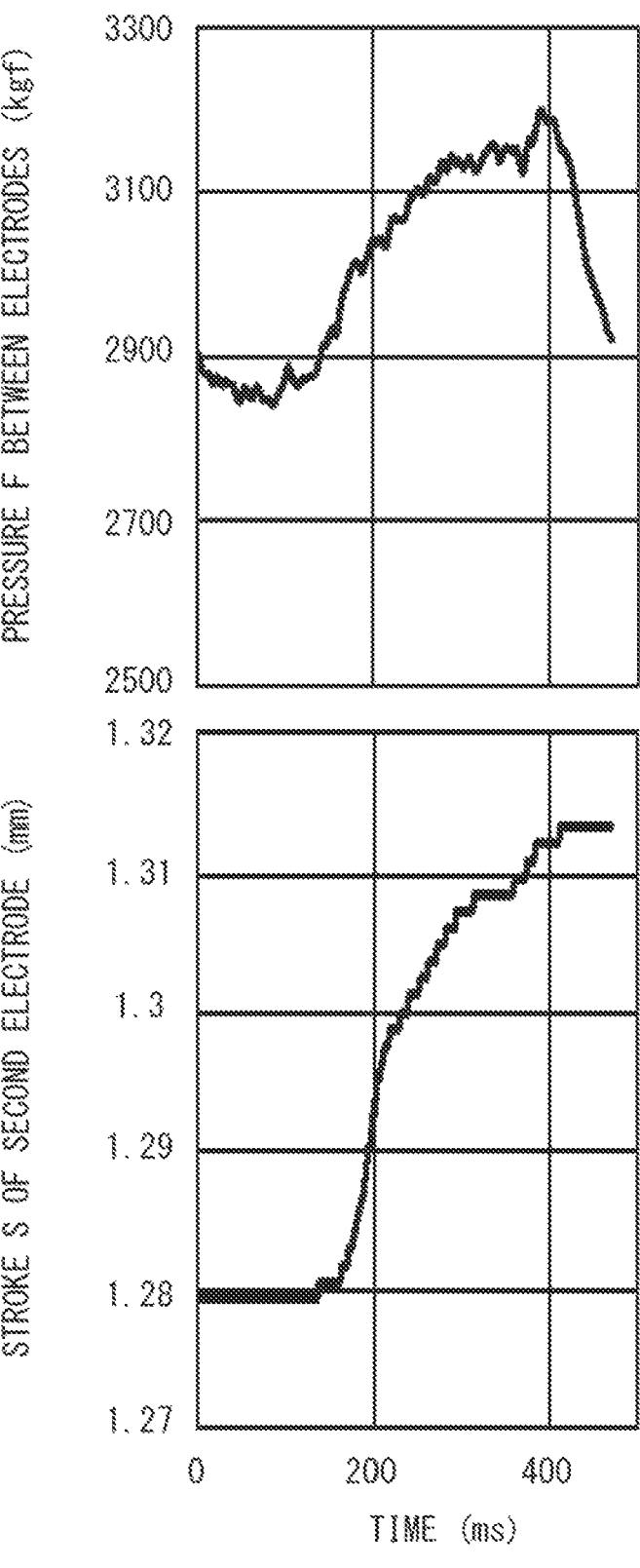
FIG. 3 shows changes in the stroke of a second electrode in the resistance spot welding and changes in a pressure between a first electrode and the second electrode.
Figure 4:
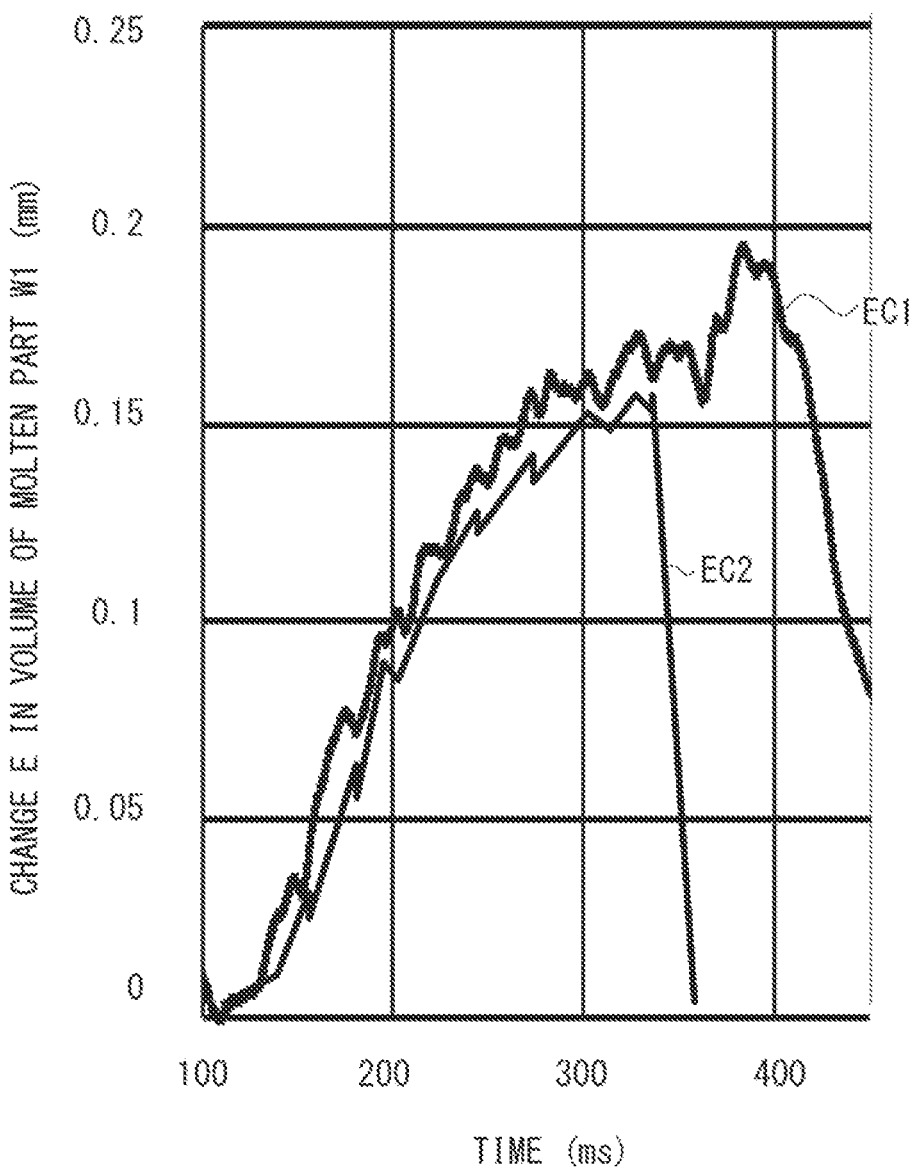
FIG. 4 shows changes in the volume of a molten part W1 in the resistance spot welding.

Next, an example in which the change in the volume of the molten part W1 is calculated will be described with reference to FIGS. 3 and 4. FIG. 3 shows changes in the stroke of the second electrode in the resistance spot welding and changes in the pressure between the first and second electrodes. The graph on the upper side in FIG. 3 shows changes in the pressure between the first and second electrodes, and the graph on the lower side shows changes in the stroke of the second electrode. The horizontal axis indicates the time in both graphs on the upper and the lower sides. FIG. 4 shows changes in the volume of the molten part W1 in the resistance spot welding.

The graph on the upper side in FIG. 3 shows an example in which the stroke S of the second electrode 12 is measured over a certain time period in order to calculate the change in the distance between the first and second electrodes 11 and 12. As shown in the graph on the upper side in FIG. 3, a period from 0 ms to about 180 ms is a phase during which a molten part W1 is generated or the thermal expansion starts, so that the stroke S of the second electrode 12 is almost constant over the time period. In a period from 180 ms to 400 ms, the molten part W1 thermally expands, so that the stroke S of the second electrode 12 increases as the time elapses. At and after 400 ms, the resistance spot welding is completed and the molten part W1 thermally contracts, so that the stroke S of the second electrode is almost constant over the time period.

The graph on the lower side in FIG. 3 shows an example in which the pressure F between the first and second electrodes 11 and 12 is measured over a certain time period in order to calculate the change in the internal stress of the molten part W1. As shown in the graph on the lower side in FIG. 3, a period from 0 ms to about 180 ms is a phase during which a molten part W1 is generated or the thermal expansion starts, so that the pressure F between the first and second electrodes 11 and 12 is almost constant over the time period. In a period from 180 ms to 400 ms, the molten part W1 thermally expands, so that the pressure F between the first and second electrodes 11 and 12 increases as the time elapses. At and after 400 ms, the resistance spot welding is completed and the molten part W1 thermally contracts, so that the pressure F between the first and second electrodes 11 and 12 decreases as the time elapses.

Note that the change in the volume of the molten part W1 is calculated by the below-shown Expression (1).

[Expression 1]

$$E = S + a \times F \qquad \text{Expression (1)}$$

Note that E is the change in the volume of the molten part W1; S is the stroke of the second electrode; a is a distortion conversion coefficient; and F is the pressure between the first and second electrodes 11 and 12.

It is possible to calculate the change in the volume of the molten part W1 by using the stroke S of the second electrode and the pressure F between the first and second electrodes 11 and 12, both of which are shown in FIG. 3, and Expression (1). FIG. 4 shows the change in the volume of the molten part W1 over the time, calculated by using the result shown in FIG. 3 and Expression (1).

Note that in Expression (1), the change in the volume of the molten part W1 is calculated by focusing on (i.e., by using) the change thereof in the z-axis direction shown in FIG. 2. Technically speaking, it is necessary to calculate the changes in the volume of the molten part W1 both in the x- and y-directions during the thermal expansion or the thermal contraction. However, since the volume of the molten part W1 changes in an isotropic manner, the change in the volume of the molten part W1 can be easily calculated by focusing only on the change in one direction, i.e., in the z-axis direction in the above-described example.

<Detection of Occurrence of Sputter 22

In the spatter detection method according to the first embodiment, an occurrence of sputter is detected based on the change in the volume of the molten part W1. The spatter detection method will be described in a more concrete manner with reference to FIG. 4. FIG. 4 shows a curve EC1 and a curve EC2. The curve EC1 is a curve showing changes in the volume E of the molten part W1 over the time, calculated by using the result shown FIG. 3 and Expression (1), and is a curve when no sputter occurs. Further, the curve EC2 is a curve showing changes in the volume of the molten part W1 over the time when sputter occurs.

In the curve EC1 shown in FIG. 4, the molten part W1 is generated and thermally expanded during a period from 0 ms to 400 ms, so that the change in the volume of the molten part W1 increases during this period. At and after 400 ms, the resistance spot welding is completed and the molten part W1 thermally contracts, so that the change in the volume E of the molten part W1 decreases.

In contrast, in the curve EC2 shown in FIG. 4, the molten part W1 is generated and thermally expands from a period from 0 ms to about 300 ms, but since the amount (e.g., the volume) of the molten part W1 is small due to an occurrence of sputter, the change in the volume of the molten part W1 is smaller than that in the curve EC1. Further, at and after about 300 ms, the molten part W1 thermally contracts, but since the amount (e.g., the volume) of the molten part W1 is small due to an occurrence of sputter, the change in the volume E of the molten part W1 sharply decreases in a shorter time than that in the curve EC1.

As described above, the change in the volume E of the molten part W1 when no sputter occurs differ from that when sputter occurs. Therefore, in the spatter detection method according to the first embodiment, it is possible to detect an occurrence of sputter based on the change in the volume E of the molten part W1 of the material to be welded M, melted by the pair of electrodes. Further, since the change in the volume E of the molten part W1 occurs regardless of the size of sputter, it is possible to accurately detect an occurrence of sputter in the spatter detection method according to the first embodiment.

Further, in regard to the thermal contraction of the molten part W1 in the curves EC1 and EC2, as shown in FIG. 4, the rate of change at which the volume of the molten part W1 decreases is larger in the curve EC2, in which sputter occurs, than in the curve EC1, in which no sputter occurs. An occurrence of sputter may be detected based on the above-described rate of change.

Figure 5:
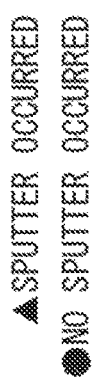
FIG. 5 shows maximum values of rates of change at which the volumes of the molten parts decrease in respective resistance spot welding performed a plurality of times.

The method for detecting an occurrence of sputter based on the rate of change at which the volume of the molten part W1 decreases will be described in a more concrete manner with reference to FIG. 5. FIG. 5 shows maximum values of rates of change at which the volumes of the molten parts decrease in respective resistance spot welding performed a plurality of times. In the example shown in FIG. 5, the horizontal axis indicates the number of times of resistance spot welding. In this example, resistance spot welding is carried out 120 times. The vertical axis indicates the maximum value of the rate of change at which the volume of the molten part decreases, and indicates the maximum value of the rate of change per 2 ms (i.e., the rate of change over 2 ms).

As shown in FIG. 5, when sputter occurs, the maximum value of the rate of change at which the volume of the molten part decreases per 2 ms is larger than a reference value SD1. Meanwhile, when no sputter occurs, the maximum value of the rate of change at which the volume of the molten part decreases per 2 ms is smaller than the reference value SD1. As described above, it is possible to determine whether sputter has occurred or not by determining whether or not the maximum value of the rate of change at which the volume of the molten part decreases per 2 ms is larger than the reference value SD1.

The reference value SD1 is, for example, a standard deviation of maximum values of rates of change at which the volume of the molten part decreases per 2 ms. Further, as the reference value SD1, a predetermined value corresponding to the type of the material to be welded may be used.

Note that although the rate of change at which the volume of the molten part decreases per 2 ms is calculated in FIG. 5, it is not limited to this example. For example, a rate of change per (i.e., over) a time longer or shorter than 2 ms may be calculated.

As described above, an occurrence of sputter is detected based on the rate of change at which the volume of the molten part W1 decreases. More specifically, the change in the volume of the molten part in the resistance spot welding is calculated based on the change in the distance between the first and second electrodes 11 and 12 and the change in the internal stress of the molten part W1. Next, the maximum value of the rate of change at which the volume of the molten part decreases is calculated. Then, an occurrence of sputter is detected according to whether or not the maximum value of the rate of change at which the volume of the molten part decreases is larger than the reference value SD1. By the above-described configuration, it is possible accurately detect an occurrence of sputter.

Note that an example in which an occurrence of sputter is detected according to whether or not the maximum value of the rate of change at which the volume of the molten part decreases is greater than the reference value SD1 is explained. However, the present disclosure is not limited to this example. For example, an occurrence of sputter may be detected by using a trained model generated by learning rates of change at which the volume of the molten part decreases.

More specifically, a learning model according to a machine learning algorithm is trained by (i.e., is made to learn) rates of change at which the volume of the molten part decreases when sputter occurs and rates of change at which the volume of the molten part decreases when no sputter occurs. The machine learning algorithm is, for example, an SVM algorithm, a nearest neighbor method, a Naive Bayes method, a decision tree, or a neural network. The trained model is generated by having a learning model learn rates of changes at which the volume of the molten part decreases.

The trained model uses a rate of change at which the volume of the molten part decreases as an input, and outputs whether or not spatter has occurred. By using the trained model as described above, it is possible improve the efficiency of the detection of occurrences of spatter.

As described above, in the spatter detection method according to the first embodiment, it is possible to detect an occurrence of spatter based on the change in the volume of the molten part W1 of the material to be welded M, melted by the pair of electrodes. Since the change in the volume E of the molten part W1 occurs regardless of the size of sputter, it is possible to accurately detect an occurrence of sputter in the spatter detection method according to the first embodiment.

<Method for Manufacturing Welded Member>

Figure 6:
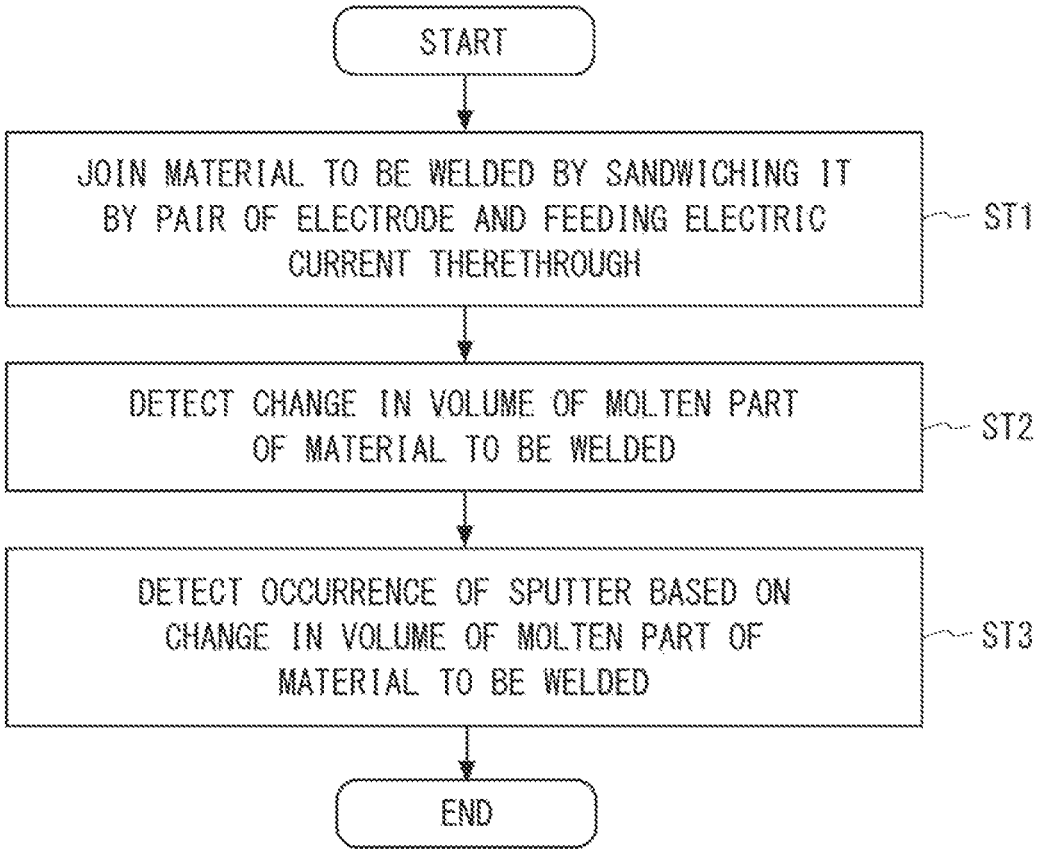
FIG. 6 is a flowchart for explaining a method for manufacturing a welded member according to a first embodiment.

Next, a method for manufacturing a welded member according to the first embodiment will be described with reference to FIG. 6. FIG. 6 is a flowchart for explaining the method for manufacturing a welded member according to the first embodiment.

Firstly, resistance spot welding in which a material to be welded, obtained by stacking a plurality of metal members on one another, is joined by sandwiching the material to be welded by a pair of electrodes and feeding an electric current therethrough (i.e., through the pair of electrodes) is performed (Step ST1). More specifically, as shown in FIG. 2, by sandwiching the material to be welded M by the first and second electrodes 11 and 12, which constitute a pair of electrodes, and feeding an electric current therethrough (i.e., through the first and second electrodes 11 and 12), a molten part W1 is generated between the metal members M1 and M2, and the material to be welded M is thereby joined.

Next, a change in the volume of the molten part W1 of the material to be welded M is detected (Step ST2). More specifically, as shown in FIGS. 2 and 3, the change in the distance between the first and second electrodes 11 and 12 can be obtained by measuring the stroke S of the second electrode 12. Further, a pressure F between the first and second electrodes 11 and 12 is measured, and a change in the internal stress IF1 of the molten part W1 is calculated from the measured pressure F. Then, as shown in FIG. 4, the change in the volume of the molten part W1 is calculated based on the change in the distance between the first and second electrodes 11 and 12 and the change in the internal stress IF1 of the molten part W1.

Next, an occurrence of sputter in the resistance spot welding is detected based on the change in the volume of the molten part W1 (Step ST3). More specifically, the rate of change at which the volume of the molten part W1 decreases is larger when sputter occurs than the rate when no sputter occurs. An occurrence of sputter is detected based on the above-described rate of change.

As described above, in the method for manufacturing a welded member according to the first embodiment, it is possible to manufacture a welded member while detecting an occurrence of sputter based on the change in the volume of the molten part W1 of the material to be welded M, melted by the pair of electrodes. Since the change in the volume of the molten part W1 occurs regardless of the size of sputter, it is possible to accurately detect an occurrence of sputter in the method for manufacturing a welded member according to the first embodiment.

From the disclosure thus described, it will be obvious that the embodiments of the disclosure may be varied in many ways. Such variations are not to be regarded as a departure from the spirit and scope of the disclosure, and all such modifications as would be obvious to one skilled in the art are intended for inclusion within the scope of the following claims.

What is claimed is:

1. A spatter detection method for detecting an occurrence of sputter in resistance spot welding, the resistance spot welding being welding in which a material to be welded, obtained by stacking a plurality of metal members on one another, is joined by sandwiching the material to be welded between a pair of electrodes and feeding an electric current therethrough, wherein the occurrence of sputter is detected based on a change in a volume of a molten part of the material to be welded, wherein the pair of electrodes comprises a first electrode, and a second electrode movable relative to the first electrode in a direction in which the metal members are stacked on one another, and the change in the volume of the molten part is calculated based on a change in a distance between the first and second electrodes, and a change in an internal stress of the molten part.

2. The spatter detection method according to claim 1, wherein the sputter is detected based on a rate of change at which the volume of the molten part decreases.

3. The spatter detection method according to claim 1, wherein the change in the volume of the molten part is calculated by Expression (1), $$E = S + a \times F \tag{1}$$

where E is the change in the volume of the molten part; S is a stroke of the second electrode; a is a distortion conversion coefficient; and F is a pressure between the first and second electrodes.

\* \* \* \* \*